United States Patent [19]
Hohmann

[11] 3,994,069
[45] Nov. 30, 1976

[54] DENTAL INSTALLATION
[75] Inventor: Eugen Hohmann, Heppenheim, Germany
[73] Assignee: Siemens Aktiengesellschaft, Berlin & Munich, Germany
[22] Filed: Mar. 27, 1975
[21] Appl. No.: 562,454

[30] Foreign Application Priority Data
Apr. 11, 1974 Germany............................ 2417890

[52] U.S. Cl. ................................................ 32/22
[51] Int. Cl.² ........................................ A61C 19/02
[58] Field of Search .......................................... 32/22

[56] References Cited
UNITED STATES PATENTS
| | | | |
|---|---|---|---|
| 3,732,622 | 5/1973 | Rackson | 32/22 |
| 3,844,039 | 10/1974 | Fleer et al. | 32/22 |
| 3,902,247 | 9/1975 | Fleer et al. | 32/22 |

*Primary Examiner*—Robert Peshock
*Attorney, Agent, or Firm*—Hill, Gross, Simpson, Van Santen, Steadman, Chiara & Simpson

[57] ABSTRACT

A dental installation for at least one dental handpiece having a compressed air motor drive which is supplied from a compressed air source through a compressed air conduit, and whose rotational speed is variable by means of a control valve controlling the compressed air through the intermediary of a pneumatic installation which, preferably, is constructed in the shape of a foot or pedal switch. In an installation of the above-mentioned type, by means of which there is achievable a technical operational simplification, in addition to one or more handpieces having compressed air motor drives, there is also provided a further handpiece with an electric motor drive. In particular, it becomes feasible to effect a subsequent equipping of a purely pneumatically designed dental apparatus, which only incorporates handpieces having pneumatic drives, with a handpiece having an electric motor drive, without necessitating any significant tampering with the apparatus.

9 Claims, 2 Drawing Figures

DENTAL INSTALLATION

FIELD OF THE INVENTION

The present invention relates to a dental installation for at least one dental handpiece having a compressed air motor drive which is supplied from a compressed air source through a compressed air conduit, and whose rotational speed is variable by means of a control valve controlling the compressed air through the intermediary of a pneumatic installation which, preferably, is constructed in the shape of a foot or pedal switch.

DISCUSSION OF THE PRIOR ART

In such a known installation, as disclosed in German Pat. No. 1,297,808, there is provided a foot-operated control arrangement for the engaging and disengaging of the compressed air motor drive (turbine), respectively, for control of the rotational speed thereof, through which there is mechanically actuated a compressed air control valve by stepping down on a foot pedal, so as to vary the flow volume for the drive. The disadvantage of such an installation resides in that when a further handpiece having an electrical motor drive, whose rotational speed is controlled by means of an electrical control element, for example a potentiometer, is to be associated with this installation, then the switching-on and control of the rotational speed of the electric motor drive must be carried out by means of an additional, separate control element, for example, in the form of a potentiometer, which is controllable either manually or by foot.

Furthermore, dental apparatus are known which include only handpieces with exclusively pneumatic drives (turbine and air motor) which, in essence, do not contain any kind of electrical service or operating components, such as magnetic valves, electrical switches or the like. The arrangements which control the pneumatic drives for these handpieces also herein, in a purely pneumatic manner, meaning, by means of an actuating element (foot pedal, pivot lever or the like), directly actuate through mechanical adjusting means (for example, tilt levers, push rods) the compressed air valves which determine the flow. Inasmuch as the compressed air motor drives are of relatively high speed (so-called high-speed drives), it is frequently desired to additionally equip such an apparatus with also a handpiece having a low speed electric motor drive (so-called low-speed drive). The additional construction can be carried out without any appreciable modification to the existing apparatus, and to dispense with the usual operation of the apparatus through the previously provided pneumatic foot-operated switch.

SUMMARY OF THE INVENTION

Accordingly, it is an object of the present invention to provide an installation of the above-mentioned type, by means of which there is achievable a technical operational simplification in addition to one or more handpieces having compressed air motor drives, there is also provided a further handpiece with an electric motor drive. In particular, it becomes feasible to effect a subsequent equipping of a purely pneumatically designed dental apparatus, which only incorporates handpieces having pneumatic drives, with a handpiece having an electric motor drive, without necessitating any significant tampering with the apparatus.

The proposed invention has the advantage that each dental apparatus having purely pneumatically operating drives, in which there are thus not present any kinds of electrical supply connections or the like, may also be easily subsequently equipped with a hand piece having an electric motor drive, and the operation of the electric motor handpiece may be carried out with the available purely pneumatic foot-operated control arrangement which is provided for the handpiece having a compressed air motor drive.

BRIEF DESCRIPTION OF THE DRAWINGS

Further advantages and details of the invention may now be ascertained from the following description of an exemplary embodiment thereof, taken in conjunction with the accompanying drawings; in which.

Detailed Description

Figure 1:
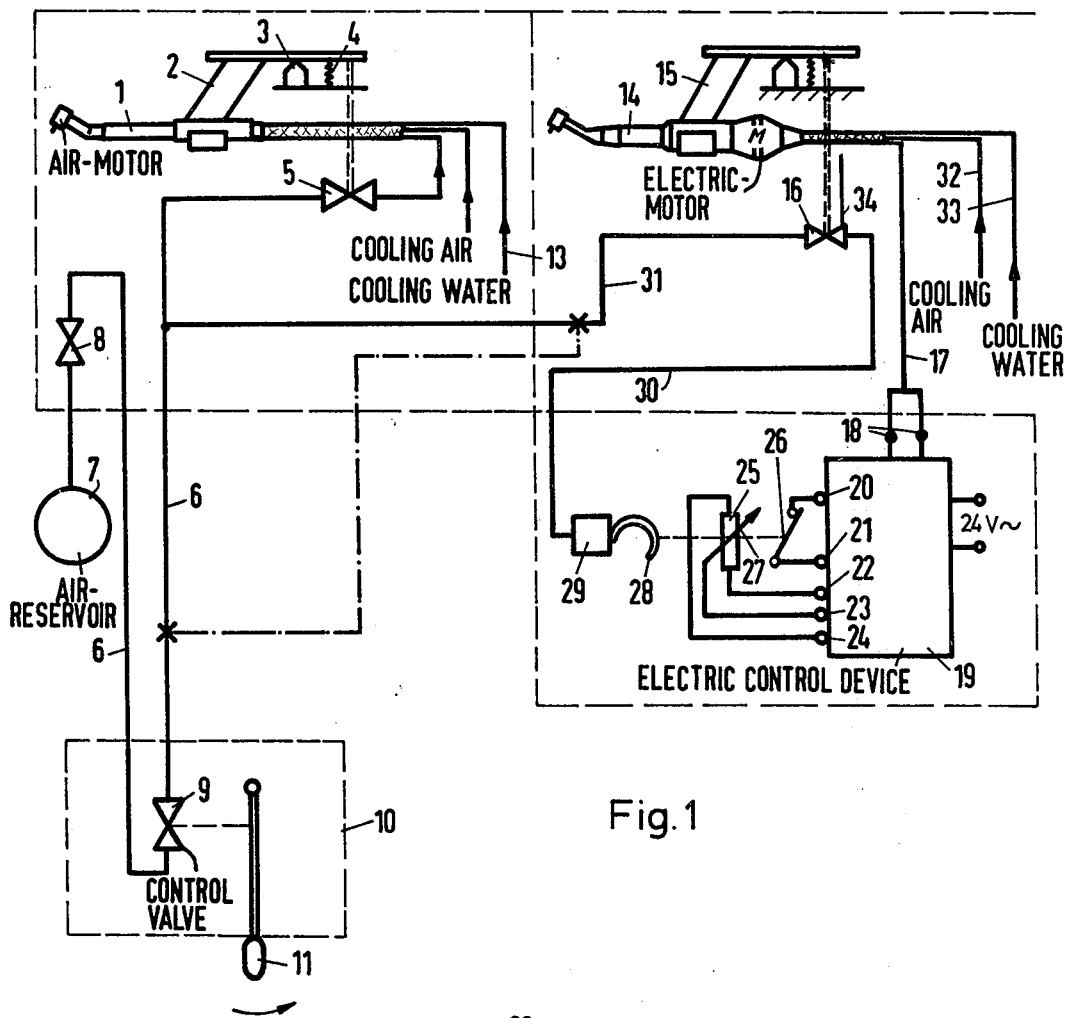
FIG. 1 illustrates a largely schematic and simplified representation of the control installation pursuant to the present invention, wherein components deemed not essential for an understanding of the invention have been omitted for purposes of clarity.

Referring now in detail to the drawing, a dental handpiece including a direct compressed air motor drive (turbine or air motor) is designated by referencce numeral 1, and is supported in a depository arrangement 2. The depository arrangement 2 is movably supported on a stationary portion 3 of an apparatus (not shown) in such a manner whereby, upon removal of the handpiece from the depository arrangement 2, the latter is readily raised through the force of a spring 4. Connected with the depository arrangement 2 by means of an adjusting element (not shown), for example, a plunger or rocker arm, is a compressed air valve 5 which is closed when the handpiece is laid down on the depository arrangement, and opened upon the handpiece begin raised. By means of the compressed air valve 5, compressed air is conveyed from air reservoir 7 through the pneumatic conduit 6 to the drive motor. Further communicating with the pneumatic conduit 6 is a pressure reduction valve 8. Reference numeral 9 designates a control valve located in the foot control arrangement identified as reference numeral 10 in the drawing. The foot control arrangement 10 is constructed in a known manner as shown, for example, in German Pat. Application No. P 22 31 234, and contains a foot-actuatable pivot lever 11 which is so connected with the valve 9 through the interposition of a mechanical adjusting element (plunger, rocker arm, pivot lever, or the like) whereby, upon displacement of the pivot lever from an initial position, the flow cross-section of the valve is constantly increased. Through a change in the flow quantity there may thus be varied the rotational speed of the compressed air motor drive within predetermined bounds.

Designated by reference numerals 12 and 13 are conduits connecting into the handpiece 1 for effecting the infeed of cooling spray air and spray water. Inasmuch as the control over these media is not essential to an understanding of the invention, for purposes of clarity they have been omitted in connection with the illustration of the control through the foot control arrangement 10. The control of these media may, for example, be effectuated in a manner as is described in the previously mentioned German Pat. No. 1,297,808.

In correspondence with the described arrangement, still further handpieces having direct compressed air motor drives may be connected thereto. The switching-in of the compressed air and the control over the through-flow is then similarly carried out by means of the common foot control arrangement 10.

Associated with the handpiece 1 having the direct compressed air motor drive is a further handpiece 14 having a direct electric motor drive (designated by M), which is adapted to be deposited in a depository arrangement 15 when not in use, as with handpiece 1, and which is connected with a valve 16.

The supply of the electrical energy to the motor is effected by means of conduits 17 are connected to the output 18 a power supply installation 19. The power supply installation 19 is supplied with a voltage $U = 24$ V. The installation further evidences additional terminals 20 through 24; the terminals 20 through 24 being connected with a variable resistance 25, or potentiometer, and the terminals 20, 21 with a switch 26 with a spacer contact. The switch contact 26, as well as the variable tap-off 27 of the variable resistance 25 are coupled with a curved bourdon tube 28 of a pneumatic-electrical transducer 29, the latter of which is connected with the valve 16 through the intermediary of a pneumatic conduit 30. The valve 16 is connected at the inlet end thereof with the pneumatic conduit 6 through a conduit 31. The conduit 31 may branch off either immediately downstream of the foot switch 10, (phantomline illustrated); or branch off in the apparatus (in which the handpieces are supported). Designated respectively by reference numerals 32 and 33 are conduits for the infeed of cooling air and cooling spray water to the handpiece 14. Also in this instance, for purposes of improved clarity, the illustration of the control over these media is omitted, since it may be carried out in a known manner. Designated by reference numeral 34 is a venting nozzle which connects into the conduit 30, and by means of which the pressure head in the conduit system may be reduced after the switching-off of the drives. The opening of the nozzle is so dimensioned that approximately 3 to 20 Nl/min air may flow out, which is sufficient for a rapid venting of the conduit 30 and the air chamber of the transducer 29. In lieu of the nozzle 34, the motor cooling air may be taken out of valve 16, wherein the cooling air conduit 32 is connected with the outlet of the valve 16.

The components 14, 15 and 17 through 27, as well as 32 and 33, constitute a known control installation for a handpiece with an electric motor drive. Details of the power supply arrangement 19, since this is within the state of the art and is described, for example, in German Pat. Application No. P 23 39 827, are not further detailed within the framework of this disclosure. It is merely pointed out that, when the switch 26 is opened and the potentiometer 25 is adjusted through variation of the tap-off 27, the output voltage at the contacts 18 is increased, so as to lead to a higher motor voltage and thereby to a higher rotational speed of the motor.

It is further noted that, in lieu of the bourdon tube, there may be also provided a differently constructed transducer, for example, it is thinkable that a cylinder-piston arrangement with a corresponding dimensioning may be provided, by means of which, in dependence upon the existing pressure in the control conduit 6, the potentiometer may be adjusted for variation of the rotational speed of the electric motor.

Figure 2:
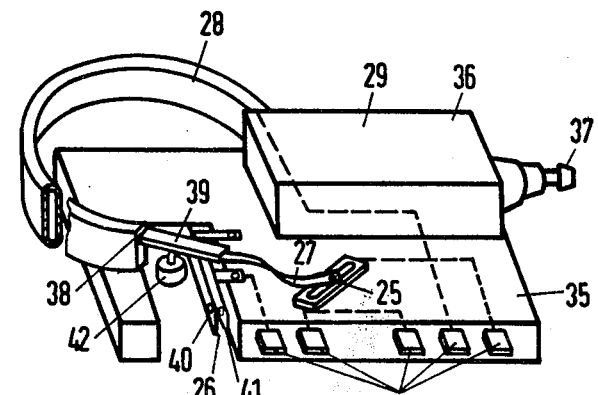
FIG. 2 perspectively illustrates details of the transducer employed in the construction of the inventive apparatus.

FIG. 2 illustrates, in a perspective view, details of the transducer 29. On a support plate 35 there is located a block 36 which evidences a pressure connector portion 37 for the connection of the pneumatic conduit identified by reference numeral 30 in FIG. 1. The pressure connecting portion 37 is connected with the curved interiorly hollow bourdon tube 28, which is soldered to the block 36. At the free end 38 of the bourdon tube 28 there is located a follower 39, onto which there is fastened the variable tap-off 27 of the variable resistance or potentiometer 25. On the support plate 37 there are also located two contact plates 40, 41 forming the switch 26, which in the initial position, in effect, for pressureless transducer 29, are pressed together by means of a pressure member 42 in the sense of a contact former. The contact plates 40, 41, as well as the tap-offs of the potentiometer 25 are provided with plug tongues 43, which project from one side of the support plate 35. Complementary to these plug tongues 43 are constructed the corresponding contacts 20 through 24 of the power supply installation 19 (FIG. 1). The entire transducer may be rapidly placed into readiness for operation through simple mounting on the power supply arrangement 19. The connection of the individual contacts to the plug tongues 42 is shown in phantom lines. For the variable intermediate tap-off 27, the contact is effected through the electrically-conductively constructed bourdon tube 28, and the similarly electrically-conductively constructed block 36.

The operation of the installation is as follows:

If, for example, the electric motor-driven handpiece 14 is removed from its repository, then the valve 16 is opened (mechanically). The handpiece is thereby in its prepared operating position. By means of deflection of the pivot lever 11, the control valve 9 in the foot control arrangement 10 is opened. The compressed air flows through conduits 6, 31 and 30 to the pressure transducer 29 and into the bourdon tube 28. At a pressure of approximately 0.2 atmosphere, the ring-shaped bourdon tube is expanded; and the contacts 40 and 41 of the switch, which are closed in their initial positions, are opened. At a further displacement, the slide contact 27 of the potentiometer 25 is displaced leading through the control electronic 19 to a change in the output voltage at the terminals 18. At full pressure, which consists of about 4 atmospheres, the highest voltage is provided to the terminals 18, and accordingly to the motor which is located in the handpiece, which corresponds to a maximum rotational speed for the motor.

In view of the function of the switch contacts which are closed in the initial position, it is also mentioned that, with the opening of the switch contacts 26, two transistors which control the motor current are closed, so that the voltage applied to the terminals is zero. At a deflected foot pedal switch the stationary or initially closed contact is opened. By means of an RC-time element, the mentioned transistors are controlled. The more the pivot lever is deflected, the larger is the pressure acting on the bourdon tube, and there more is the displacement of the potentiometer. The transistors which control the motor current always open more thereby, so as to lead to an increase in the voltage at the motor, and thereby to an increase in its rotational speed.

While there has been shown what is considered to be the preferred embodiment of the invention, it will be obvious that modifications may be made which come within the scope of the disclosure of the specification.

What is claimed is:

1. In a dental installation including at least one dental handpiece having a compressed air motor drive; a compressed air source; a pneumatic conduit connecting said compressed air source to said motor drive; a control valve for controlling the compressed air flow; and a control arrangement comprising a foot-operated switch for controlling said control valve so as to vary the rotational speed of said motor drive, the improvement comprising: at least one handpiece having an electric motor drive; electrical switch means for selectively activating and deactivating controlling electric motor drive; and electrical control element for cntrolling the rotational speed of said electric motor drive and comprising a variable resistance; means responsive to the compressed air controlled by said control valve for said compressed air motor drive for exerting an influence over the electrical control means for controlling the rotational speed of said electric motor drive; closure means in each of the control circuits of both the compressed air motor drive and electric motor drives for preventing the activation of one said drive during the operation of the other drive and reversely; said closure means in the pneumatic control circuit comprising a pneumatic flow valve for releasing the compressed air to the compressed air motor during operation of the handpiece having the compressed air motor drive; said closure means in the electrical control circuit comprising a second flow valve associated with the handpiece having said electric motor drive, the inlet side of said second flow valve being connected to said pneumatic conduit intermediate said control valve and said second flow valve; a pneumatic-electrical transducer being connected to the outlet side of said second flow valve, said transducer having a portion variable dependent upon the compressed air connected to said electrical switch means and to said electrical control element whereby, upon said transducer being subjected to compressed air, the electrical circuit of the electrical motor is closed and with an increasing air pressure said control element is varied so as to effect an increase in the voltage at the terminals of said electric motor.

2. An installation as claimed in claim 1, said electrical control element comprising a potentiometer.

3. An installation as claimed in claim 1, said means for exerting an influence over the electrical control means being connected to said electrical switch means for activation of said electrical motor drive.

4. An installation as claimed in claim 1, said means for exerting an influence over the electrical control means being spatially separated from said pneumatic control arrangement.

5. An installation as claimed in claim 1, comprising a support element, said transducer, electrical switch means and electrical control element being collectively mounted on said support element so as to constitute a functional unitary structure.

6. An installation as claimed in claim 5, said support element including readily detachable contact means for connection to a power supply means for said electric motor drive.

7. An installation as claimed in claim 6, said contact means comprising plug contacts.

8. An installation as claimed in claim 6, said support means being adapted to receive the entire power supply means for said electric motor drive.

9. In a dental installation including at least one dental handpiece having a compressed air motor drive; a compressed air source; a pneumatic conduit connecting said compressed air source to said motor drive; a control valve for controlling the compressed air flow; and a control arrangement comprising a foot-operated switch for controlling said control valve so as to vary the rotational speed of said motor drive, the improvement comprising: at least one handpiece having an electric motor drive; electrical switch means for selectively activating and deactivating said electric motor drive; an electrical control element for controlling the rotational speed of said electric motor drive; means responsive to the compressed air controlled by said control valve for said compressed air motor drive for exerting an influence over the electrical control means for controlling the rotational speed of said electric motor drive; closure means in each of the control circuits of both the compressed air motor drive and electric motor drives for preventing the activation of one said drive during the operation of the other drive and reversely; said closure means in the pneumatic control circuit comprising a pneumatic flow valve for releasing the compressed air to the compressed air motor during operation of the handpiece having the compressed air motor drive; said closure means in the electrical control circuit comprising a second flow valve associated with the handpiece having said electric motor drive, the inlet side of said second flow valve being connected to said pneumatic conduit intermediate said control valve and said second flow valve; a pneumatic-electrical transducer being connected to the outlet side of said second flow valve, said transducer having a portion variable dependent upon the compressed air connected to said electrical switch means and to said electrical control element whereby, upon said transducer being subjected to compressed air, the electrical circuit of the electrical motor is closed and with an increasing air pressure said control element is varied so as to effect an increase in the voltage at the terminals of said electric motor; said transducer comprising a curved bourden tube; a variable resistance having a variable tap-off, said tap-off being connected to a free end of said bourdon tube; and a follower for respectively opening and closing said electrical switch means being connected to said free end of the bourdon tube.

* * * * *